United States Patent [19]

Lu et al.

[11] Patent Number: 5,284,657
[45] Date of Patent: Feb. 8, 1994

[54] COMPOSITIONS AND METHODS FOR THE SUBLINGUAL OR BUCCAL ADMINISTRATION OF THERAPEUTIC AGENTS

[75] Inventors: Mou-Ying F. Lu, Lake Bluff; Thomas L. Reiland, Gages Lake, both of Ill.

[73] Assignee: Abbott Laboratories, Abbott Park, Ill.

[21] Appl. No.: 983,111

[22] Filed: Nov. 30, 1992

Related U.S. Application Data

[63] Continuation of Ser. No. 750,843, Aug. 26, 1991, abandoned.

[51] Int. Cl.$^5$ .............................................. A61K 37/54
[52] U.S. Cl. .................................. 424/435; 424/427; 424/428; 424/429
[58] Field of Search ...................... 424/94.62, 427, 428, 424/429, 435; 514/15, 800, 912, 2, 803; 435/180, 182, 201; 623/4, 5; 530/313; 930/10, 21, 130, DIG. 695

[56] References Cited

U.S. PATENT DOCUMENTS

| | | | |
|---|---|---|---|
| 4,244,946 | 1/1981 | Rivier et al. | 514/15 |
| 4,382,922 | 5/1983 | Rivier et al. | 514/15 |
| 4,632,979 | 12/1986 | Coy et al. | 530/313 |
| 4,801,577 | 1/1989 | Nestor, Jr. et al. | 514/15 |

Primary Examiner—Thurman K. Page
Assistant Examiner—C. Azpuru
Attorney, Agent, or Firm—Jerry F. Janssen

[57] ABSTRACT

Pharmaceutical compositions for the sublingual or buccal administration of therapeutic agents (particularly polypeptides) which are normally degraded upon oral administration comprise such a therapeutic agent, a solvent, optionally a cosolvent and/or hydrogel, and an oral mucosal membrane transport enhancing agent which is selected from the group consisting of essential and volatile oils and inorganic and organic acids.

11 Claims, 4 Drawing Sheets

COMPOSITIONS AND METHODS FOR THE SUBLINGUAL OR BUCCAL ADMINISTRATION OF THERAPEUTIC AGENTS

This application is a continuation of U.S. Patent application Ser. No. 07/750,843 filed Aug. 26, 1991, which is abandoned.

TECHNICAL FIELD OF THE INVENTION

The present invention relates to pharmaceutical compositions and a method of using such compositions. More particularly, the present invention concerns pharmaceutical compositions useful for the sublingual or buccal administration of therapeutic agents which are otherwise degraded by enzymatic or protiolytic action when administered orally, and to a method of using such compositions.

BACKGROUND OF THE INVENTION

Orally administered therapeutic agents are rapidly transported to the stomach and small intestine for absorption across gastro-intestinal mucosal membranes into the blood. The efficiency of absorption of a therapeutic agent (i.e. the ratio of the amount entering the blood to the amount administered) following oral administration of many drugs can be low because of several factors which serve to metabolize the administered chemical. Low absorption efficiency is particularly problematic with polypeptide therapeutic agents.

The gastrointestinal tract secretes a variety of agents that metabolize polypeptides. Exemplary of such catabolic agents are pepsin, trypsin, chymotrypsin, carboxypolypeptidases, aminopolypeptidases and dipeptidases. Polypeptides that escape catabolism in the stomach and small intestine are transported across the cells lining the gastrointestinal tract into the portal circulation, which carries absorbed polypeptides to the liver. Absorbed polypeptides are subject to further degradation by a myriad of hepatic metabolic events. Such hepatic degradation of absorbed materials from the blood before such materials enter the general systemic circulation is known in the pharmaceutical art as the "first pass effect".

As a result of these factors causing low absorptive efficiency of orally administered therapeutic agents, particularly polypeptides, if the choice of the route of administration is the oral route, it is necessary to administer large dosages of such polypeptides. This is costly in many cases and inefficient. Alternatively, such therapeutic agents can be administered via other routes such as intravenously, subcutaneously or intraperitoneally. These alternate routes are all invasive by nature and can involve pain and discomfort to a subject. There is, therefore, a pressing need for new, efficient, cost-effective and non-invasive methods and compositions for the administration to patients of therapeutic agents which would be otherwise degraded if administered orally.

The present invention provides novel compositions and methods for the sublingual administration of therapeutic agents.

BRIEF DESCRIPTION OF THE DRAWINGS

In the drawings, which form a part of this disclosure.

BRIEF SUMMARY OF THE INVENTION

In its principal aspect, the present invention provides liquid compositions for the sublingual or buccal administration of therapeutic agents which are normally degraded upon oral administration, especially polypeptides, comprising said therapeutic agent and a carrier which comprises a solvent system and an oral mucosal membrane transport enhancing agent. The solvent system comprises a non-toxic alcohol which is from about 50 percent to about 95 percent w/v of the total volume of the carrier. The balance of the carrier comprises from about 0.5 percent w/v to about 20 percent w/v, based upon the total volume of the carrier, of a mucosal membrane transport enhancing agent and, optionally, a cosolvent and/or a hydrogel. The cosolvent, when present, comprises from about 5 percent w/v to about 50 percent w/v of the carrier, and the optional hydrogel, when present, comprises from about 1 percent w/v to about 5 percent w/v of the carrier. The oral mucosal membrane transport enhancing agent is selected from the group consisting of essential and volatile oils and pharmaceutically acceptable, non-toxic inorganic or organic acids, and comprises between about 0.5 percent w/v and 50 percent w/v of the carrier.

In another aspect, the present invention provides a method for the sublingual or buccal administration of a therapeutic agent, particularly a polypeptide, to a patient comprising preparing a liquid composition of this invention and administering said liquid composition under the tongue of the patient.

DETAILED DESCRIPTION OF THE INVENTION

The liquid compositions of the present invention are particularly suited for the sublingual or buccal administration of sensitive therapeutic agents, particularly polypeptide therapeutic agents, which are normally degraded upon oral administration. As used herein, the term "polypeptide" means a compound comprising a sequence of amino acid residues connected by peptide linkages. Polypeptides can have from 2 to about 150 amino acid residues. Thus, for the purpose of the present invention, polypeptide is inclusive of what is generally referred to in the art as peptide, polypeptide and protein. The amino acid residue sequence can be connected to lipids or carbohydrates in the form of lipoproteins or glycoproteins. Preferably, polypeptides used in the present invention are drugs, medicaments and other agents having a pharmacological or physiological action in an animal subject. Representative polypeptides which can be sublingually or buccally administered employing the formulations of the present invention include growth hormone, insulin, leutenizing hormone releasing hormone (5-oxo-Pro-His-Trp-Ser-Tyr-Gly-Leu-Arg-Pro-Gly-NH$_2$, LHRH -Sequence ID No. 1), oligopeptide therapeutic agents of from seven to ten amino acid residues which control the release of LHRH such as and 5-oxo-Pro-His-Trp-Ser-Tyr-D-Leu-Leu-Arg-Pro-N-ethylamide (leuprolide-Sequence ID No. 2), cholecystokinin (Lys-Ala-Pro-Ser-Gly-Arg-Met-Ser-Ile-Val-Lys-Asn-Leu-Gln-Asn-Leu-Asp-Pro-Ser-Arg-Ile-Ser-Asp-Arg-Tyr(SO$_3$H)-Met-Gly-Trp-Met-Asp-Phe-NH$_2$, CCK-Sequence ID No. 3)) and and therapeutic agents which control the release of CCK such as BOC-Trp-$\epsilon$-(2-methylphenylaminocarbonyl)Lys-Asp-(N-methyl)Phe-NH$_2$ (Sequence ID No. 4).

The compositions of this invention comprise the therapeutic agent dissolved or dispersed in a carrier which comprises a solvent, an optional cosolvent, an optional hydrogel, and an oral mucosal membrane transport enhancing agent. The solvent comprises from about 50 percent w/v to about 95 percent w/v, preferably from about 55 percent w/v to about 80 percent w/v of the carrier of a non-toxic alcohol. Non-toxic alcohols useful in the formulations of the present invention are selected from those well known in the art and include ethanol, isopropanol, stearyl alcohol, propylene glycol, polyethylene glycol (preferably having a molecular weight of up to about 650 daltons), and the like. Non-toxic alcohols for use in pharmaceutical formulations are well known in the art (cf., for example, Handbook of Pharmaceutical Excipients, pub. by the American Pharmaceutical Association and The Pharmaceutical Society of Great Britain (1986)). Preferably, the non-toxic alcohol is ethanol. Most preferably, the non-toxic alcohol is ethanol and is present at a concentration of about 80 percent w/v of the carrier.

The cosolvent is selected from water or a pharmaceutically acceptable oil. Suitable oils for use in the compositions of this invention include mineral oil, Neobee TM oil, olive oil, sunflower oil, corn oil, peanut oil and the like.

Hydrogels suitable for use in the compositions of this invention include hydroxypropyl cellulose, hydroxypropyl methyl cellulose, sodium carboxymethylcellulose (CMC), polyacrylic acid, poly(methyl methacrylic acid), and the like. When present in the compositions of this invention, the hydrogel comprises from about 0.1 to about 50 percent w/v of the carrier.

The oral mucosal membrane transport enhancing agent is included in the compositions of the present invention to facilitate the absorption of the therapeutic agent across the mucosal tissues in the oral cavity and directly into the blood stream of the subject. Tissue transport enhancing agents suitable for use in the present compositions are selected from essential or volatile oils or from non-toxic, pharmaceutically acceptable inorganic and organic acids.

Essential or volatile oils which may be employed in the compositions are selected from peppermint oil, spearmint oil, menthol, pepper oil, eucalyptus oil, cinammon oil, ginger oil, fennel oil, dill oil and the like. The essential or volatile oil, when employed as the oral mucosal membrane transport enhancing agent in the compositions of the present invention is present in a concentration ranging between about 0.5 percent w/v and 50 percent w/v of the carrier. The preferred essential oil is peppermint oil, present in a concentration of between about 1 percent w/v and 5 percent w/v of the carrier.

Suitable inorganic and organic acids are selected from hydrochloric acid, phosphoric acid, aromatic and aliphatic monocarboxylic or dicarboxylic acids of from two to thirty carbon atoms such as acetic acid, citric acid, lactic acid, oleic acid, linoleic acid, lauric acid, plamitic acid, benzoic acid, salicylic acid, and the like. By the term "aromatic" carboxylic acid is meant any acid which contains the 6-membered carbocyclic ring system characteristic of benzene, and by the term "aliphatic" carboxylic acid is meant any acid which contains a straight-chain or branched chain saturated or unsaturated hydrocarbon backbone. The preferred organic acid in compositions of this invention is benzoic acid. Liquid compositions containing benzoic acid are known to enhance the bioavailability of polypeptides in such compositions when administered sublingually (See Example 3).

When the compositions of the present invention contain an acid as the oral mucosal membrane enhancing agent, the pH of the composition preferably ranges between about pH 3.0 and about pH 7.0. The pH of the compositions may be adjusted or maintained by the use of pharmaceutically acceptable, non-toxic buffer systems generally known in the art. The selection of a particular acid is dependent inter alia upon the nature of the anionic component of the acid. Thus, the subject being administered the liquid composition of the invention may be in need of phosphate, chloride, lactate and the like. Conversely, the administration of a particular anion may be contraindicated in some subjects. The concentration of acid in the liquid compositions of the present invention is dependent upon the nature of the acid (i.e., pk and dissociation constant) as well as the desired pH. When the acid is benzoic acid, a preferred concentration is from about 4 to about 10 percent by weight.

The liquid composition can be formulated into a liquid spray, a liquid drop, a gel or a paste. The desired consistency is achieved by including in the liquid composition one or more hydrogels, substances that absorb water and produce gels of varying viscosity. Hydrogels suitable for use in pharmaceutical preparations are well known in the art. See, e.a., Handbook of Pharmaceutical Excipients, pub. by The American Pharmaceutical Association and The Pharmaceutical Society of Great Britain (1986) and Handbook of Water-Soluble Gums and Resins, ed. by R. L. Davidson, McGraw-Hill Book Co., New York, N.Y. (1980).

Suitable hydrogels for use in the compositions of this invention include hydroxypropyl cellulose, hydroxypropyl methyl cellulose, sodium carboxymethyl cellulose, polyacrylic acid, poly(methyl methacrylic acid) (PMMA). Preferred hydrogels are cellulose ethers such as hydroxyalkylcellulose and hydroxyalkylalkyl-cellulose compounds. A preferred hydroxyalkylcellulose is hydroxypropyl cellulose. Hydroxypropyl cellulose is commercially available in a wide range of viscosity grades sold under the tradename Klucel TM (Hercules, Ltd., London, England). The concentration of the hydroxyalkylcellulose is dependent upon the particular viscosity grade used and the desired viscosity of the liquid composition. For example, where the desired viscosity is less than about 1000 centipoise (cps), hydroxypropyl cellulose having an average molecular weight of about 60,000 daltons (i.e., Klucel EF TM) can be used. Where the desired viscosity is from about 1000 to about 2500 cps, higher viscosity grades of hydroxypropyl cellulose can be used (i.e., Klucel LF TM and Lucel GF TM). Preferably, the concentration of hydroxypropyl cellulose is from about 1 to about 5 percent w/v and, more preferably from about 2 to about 3 percent w/v of the carrier.

Hydroxyalkylalkylcellulose ethers are a class of water-soluble hydrogels derived from etherification of cellulose. As used herein in reference to this class of hydrogels, the term "alkyl" means $C_1-C_6$ alkyl where alkyl refers to linear or branched chains having 1 to 6 carbon atoms, which can be optionally substituted as herein defined. Representative alkyl groups include methyl, ethyl, propyl, isopropyl, butyl, pentyl, hexyl and the like.

Exemplary hydroxyalkylalkylcelluloses are hydroxypropylmethyl cellulose, hydroxyethylmethyl cellulose and hydroxybutylmethyl cellulose. Hydroxypropylmethyl cellulose (HPMC) is preferred. HPMC is commercially available (i.e., Aldrich Chem. Co., Ltd. Dorset, England and Dow Chem. Co., Midland, Mich., USA) in a wide range of viscosity grades. In addition to increasing viscosity, hydroxyalkylalkylcelluloses can serve as a stabilizing, suspending and emulsifying agent. The concentration of hydroxyalkylalkylcellulose in a liquid composition of this invention is dependent inter alia on its intended use (i.e., stablizer, emulsifer, viscosity-increasing agent) and its viscosity grade.

In one preferred embodiment of the present invention, the formulation comprises between 1 mg/ml and 100 mg/ml of an agent effective to control the release of leutenizing hormone releasing hormone or a pharmaceutically acceptable salt thereof; a carrier comprising between about 55 and about 80 percent w/v ethanol, about 2 to about 5 percent w/v of hydroxypropyl cellulose hydrogel; and an oral mucosal membrane transport enhancing agent comprising about 10 and about 25 percent w/v benzoic acid; all percentages based upon the total volume of carrier.

In another preferred embodiment of the present invention, the formulation comprises between 1 mg/ml and 100 mg/ml of an agent effective to control the release of leutenizing hormone releasing hormone or a pharmaceutically acceptable salt thereof; a carrier comprising between about about 55 and about 80 percent w/v ethanol, about 2 to about 5 percent w/v of hydroxypropyl cellulose hydrogel; and an oral mucosal membrane transport enhancing agent comprising between about 5 and about 20 percent w/v benzoic acid and between about 1 to about 5 percent w/v peppermint oil; all percentages based upon the total volume of carrier.

In another aspect, the present invention comprises a method of sublingually administering a therapeutic agent, preferably a polypeptide, to a patient comprising preparing a liquid composition of said therapeutic agent and an aqueous-alcohol solvent having from about 50 to about 80 percent by volume of a non-toxic alcohol and a pH from about 4.0 to about 7.0 and administering an effective amount of said liquid composition to the underside of the tongue of said patient. The liquid compositions contemplated for use in this method are those set forth above.

The liquid composition is administered to the patient under the tongue. The sublingual mucosae, located on the underside of the tongue, provide expeditious entry of the polypeptide-containing liquid composition into the general bloodstream through the sublingual tributary veins. The therapeutic agent is first absorbed through the sublingual mucosae into the sublingual veins. From there, the polypeptide is pumped into the right side of the heart and then into the lungs where the blood is oxygenated. From there the oxygenated blood would carry the therapeutic agent back into the left side of the heart and out through the systemic arteries for distribution throughout the body.

The liquid composition can be administered under the tongue by placing one or more drops underneath the tongue or by spraying the underside of the tongue with a preselected volume of the liquid composition. Preferably, the administered volume, either drops or spray, is less than about 1 ml.

The following Examples are provided to enable one skilled in the art to practice the present invention and are merely illustrative of the invention. They should not be read as limiting the scope of the invention as it is defined by the appended claims.

EXAMPLE 1

Bioavailability of Leuprolide Acetate Administered Sublinaually

The liquid compositions of Table 1 were prepared by dissolving the synthetic polypeptide leuprolide acetate in the liquid compositions such that the leuprolide acetate concentration was about 50 mg/ml. Leuprolide acetate has the formula: 5-oxo-L-prolyl-L-histidyl-L-tryptophanyl-L-seryl-L-tyrosyl-D-leueyl-L-leueyl-L-arginyl-L-propyl-ethylamide monoacetate.

TABLE 1

| | | |
|---|---|---|
| A. | Leuprolide acetate | 50 mg/ml. |
| | Urea | 10% (w/v) |
| | Klucel EF TM | 2% (w/v) |
| B. | Leuprolide acetate | 50 mg/ml |
| | Benzoic acid | 5% (w/v) |
| | Klucel EF TM | 2% (w/v) |
| | Ethanol | 50% (w/v) |
| C. | Leuprolide acetate | 50 mg/ml |
| | Klucel EF TM | 2% (w/v) |
| D. | Leuprolide acetate | 50 mg/ml |
| | Hydroxypropyl cyclodextrin | 20% (w/v) |
| | Klucel EF TM | 2% (w/v) |
| E. | Leuprolide acetate | 50 mg/ml |
| | Ethanol | 80% (v/v) |
| | Klucel EF TM | 2% (w/v) |
| F. | Leuprolide acetate | 50 mg/ml |
| | Peppermint oil | 10% (v/v) |
| | Ethanol | 80% (v/v) |
| | Klucel EF TM | 2% (w/v) |
| G. | Leuprolide acetate | 50 mg/ml |
| | Urea | 10% (w/v) |
| | L-arginine HCl | 20 mg/ml |
| | Klucel EF TM | 2% (w/v) |

The liquid compositions were sublingually administered to dogs by placing 0.1 ml/10 Kg. body weight between the underside of the tongue and the bottom of the oral cavity. In this way, each dog received a dose of leuprolide acetate equal to 0.5 mg/kg. body weight.

The plasma level of leuprolide was determined before and 0.25, 0.5, 1, 2, 4, and 6 hours after sublingual administration of the liquid compositions. The results of these studies are summarized in FIG. 1 and Table 2.

TABLE 2

| Composition From Table 1 | AUC (0–6 hours) | % Bioavailability* |
|---|---|---|
| A | 34 | 2.1 |
| B | 318 | 19.4 |
| C | 51 | 3.1 |
| D | 17 | 1.1 |
| E | 353 | 21.5 |
| F | 1385 | 84.5 |
| G | 21 | 1.3 |

*Bioavailability is calculated based on iv data

In this and subsequent Examples, bioavailability is calculated and expressed either in terms of Area Under Curve (AUC) or as percent (%) bioavailability. AUC is determined by calculating the area under the curve of plots of time (X-axis) versus plasma concentration (Y-axis) of the administered polypeptide. Typically, AUC is determined over a 6 (0–6) or 8 (0–8) hour period. Percent bioavailability is calculated as the ratio $$\frac{AUC \text{ for sublingual administration}}{AUC \text{ for the same dose administered sc or iv}} \times 100$$

Increases in AUC and/or bioavailability indicate increased bioavailability of the administered polypeptide.

Figure 1:
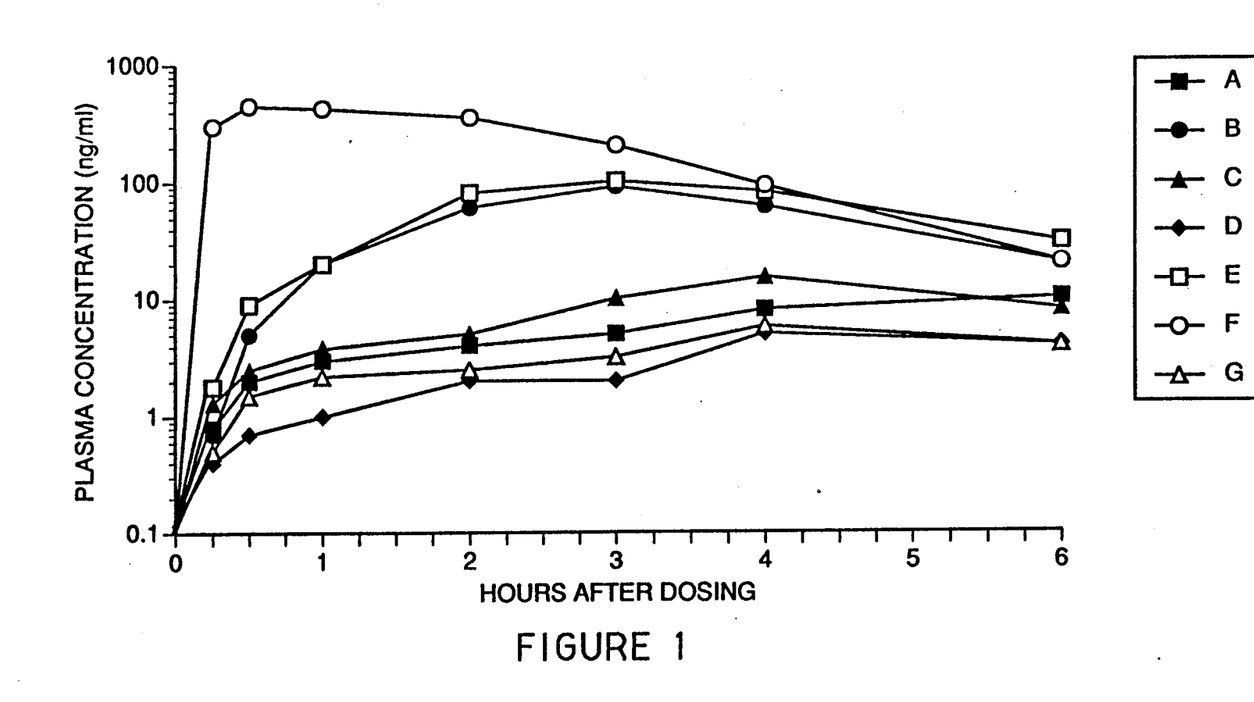
FIG. 1 is a plot of plasma leuprolide concentration vs. time following the sublingual administration of seven (A–G) different liquid compositions containing 50 mg/ml of the leutenizing hormone releasing hormone (LHRH) agent leuprolide acetate. Anesthetized dogs were administered 0.1 ml/10 kg body wt of compositions A–G of Table 1 and the plasma levels of leuprolide determined by RIA at the indicated times.

The data in FIG. 1 and Table 2 show that ethanol in concentrations from 50 (compositions B, Table 1) to 80 percent by volume (compositions E and F, Table 1) increased the bioavailability of sublingually administered leuprolide.

EXAMPLE 2

Effects of Ethanol on Bioavailability Of Sublingually Administered Leuprolide Acetate These studies were designed to test the effects of ethanol concentration on the bioavailability of sublingually administered leuprolide acetate. Liquid compositions comprising 2 percent by weight peppermint oil, 2.5 percent by weight Klucel LF™, 50 mg/ml leuprolide acetate and an aqueous-alcohol solvent having 0, 50, 65 or 80 percent by volume ethanol were prepared.

Figure 2:
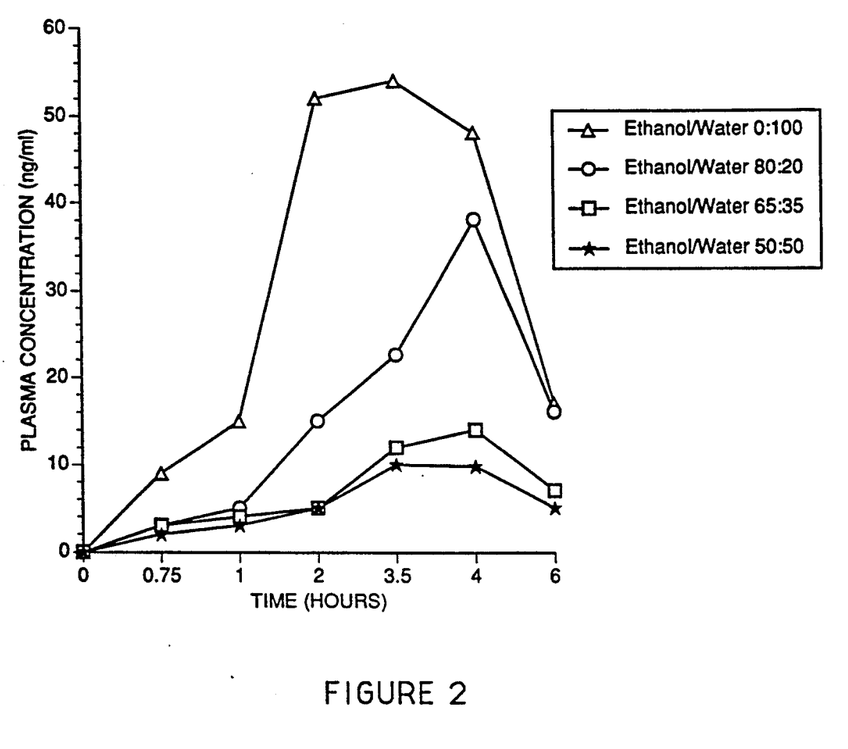
FIG. 2 is a plot of plasma leuprolide concentration vs. time following the sublingual administration of liquid compositions comprising 2.5 percent by weight Klucel LF⊥, an aqueous-alcohol solvent having 0 percent (EtOH:H20 0:100), 50 percent (EtOH:H20 50:50) 65 percent (EtOH:H20 65:35) or 80 (EtOH:H20 80:20) by volume ethanol (EtOH). The dose of administered leuprolide acetate and the measurement of plasma leuprolide concentration are the same as described for FIG. 1.

Aliquots of these liquid compositions (0.1 ml/10 Kg. body weight) were sublingually administered to anesthetized dogs using a drop or spray dispenser. Plasma levels of leuprolide were measured by RIA in venous blood samples before and 0.33, 0.67, 1, 2, 3, 4, 6 and 8 hours after administration. The results of these studies are shown in FIG. 2 and Table 3.

TABLE 3

| Ethanol (%) (w/v) | Bioavailability (%)* |
|---|---|
| 80 | 8.7 |
| 65 | 5.0 |
| 50 | 2.0 |
| 0 | 2.0 |

*Bioavailability was calculated based on the sc absorption.

The data in FIG. 2 and Table 3 show that ethanol concentration causes a dose-dependent increase in the bioavailability of sublingually administered leuprolide.

EXAMPLE 3

Effects of pH on Bioavailability Of Sublingually Administered Leuprolide Acetate Liquid compositions were prepared to comprise 50 mg/ml leuprolide acetate, 2.5 percent by weight HPMC, an aqueous-alcohol solvent having 80 percent by volume ethanol and 0, 5 or 10 percent by weight benzoic acid. The pH's of liquid compositions having 0, 5 or 10 percent by weight benzoic acid were about 6.8, 5.6 and 4.4 respectively. The results of these studies are shown in FIG. 3.

Figure 3:
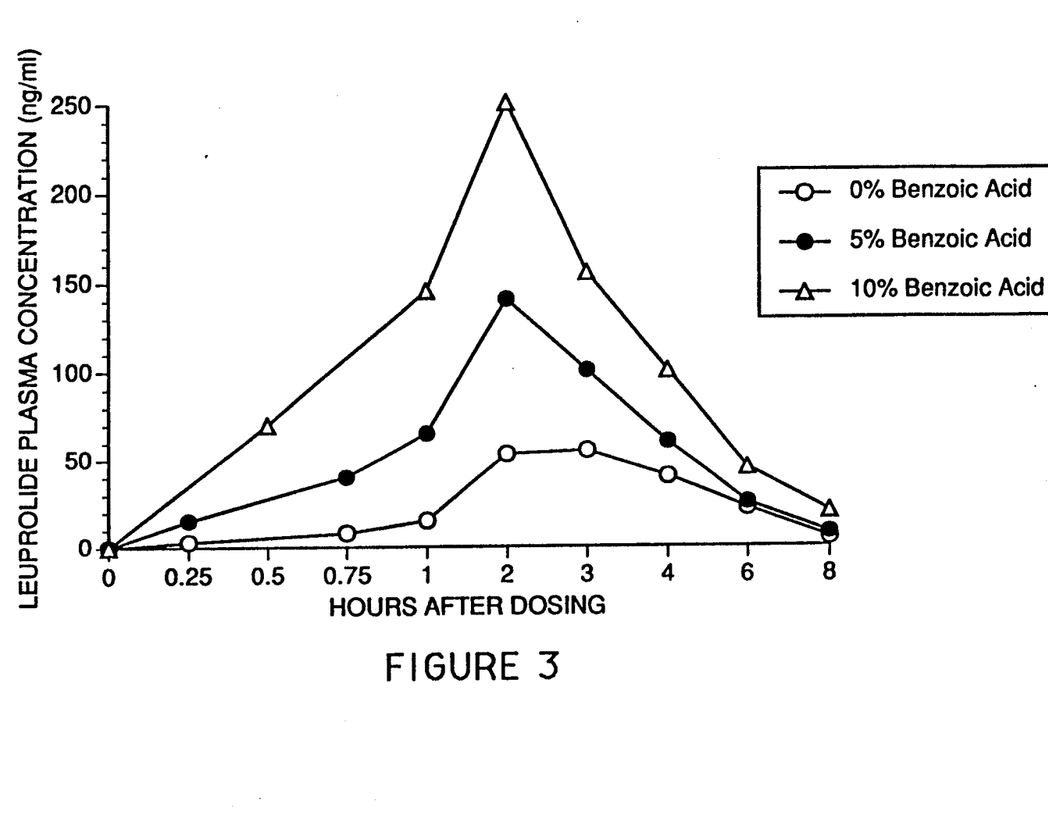
FIG. 3 is a plot of plasma leuprolide concentration vs. time following the sublingual administration of a liquid composition comprising 50 mg/ml leuprolide acetate, 2.5 percent by weight hydroxypropylmethyl cellulose (HPMC), an aqueous-alcohol solvent having 80 percent by volume ethanol and 0, 5 or 10 percent by weight benzoic acid. The dose of administered leuprolide acetate and the measurement of plasma leuprolide concentration are the same as described for FIG. 1.

The data in FIG. 3 show that the bioavailability of leuprolide is directly proportional to benzoic acid concentration. Additional studies were performed to show that the effects of benzoic acid on bioavailability were due to changes in pH rather than an inherent property of benzoic acid per se. Liquid compositions comprising 50 mg/ml leuprolide acetate, 2 percent by weight peppermint oil, an aqueous-alcohol solvent having 65 percent by volume ethanol and 4 percent by weight benzoic acid were prepared. In one such composition the pH value was adjusted to a value of about 7.0 with NaOH. In another such composition, the pH value was not adjusted and was about 5.6.

The liquid compositions were sublingually administered to dogs (0.1 ml/10 kg body wt) and the plasma levels of leuprolide measured over 8 hours. The results of this study are summarized in Table 4.

TABLE 4

| Ethanol (% w/v) | Peppermint Oil (% w/v) | Benzoic Acid (% w/v) | pH | Percent Bioavailability* |
|---|---|---|---|---|
| 65/35 | | | 6.2 | 5.0 |
| 65/35 | 2 | | 6.2 | 16.9 |
| 65/35 | 2 | 4 | 5.6 | 24.5 |
| 65/35 | 2 | 4 | 7.0 (Adjusted) | 2.7 |

*Bioavailability was calculated based on the sc absorption.

The data in Table 4 show that the enhanced bioavailability associated with benzoic acid is a function of pH.

EXAMPLE 4

Effects Of Peppermint Oil On The Bioavailability Of Sublingually Administered Leuprolide Acetate Liquid compositions comprising 50 mg/ml leuprolide acetate, an aqueous-alcohol solvent having 80 percent by volume ethanol and 0, 0.5, 2, 2.5, 5 and 10 percent by volume peppermint oil were prepared and sublingually administered to dogs at a dose of 0.1 ml/10 kg body weight. Plasma leuprolide levels were monitored for 8 hours following administration. The results of this study are shown in FIG. 4.

Figure 4:
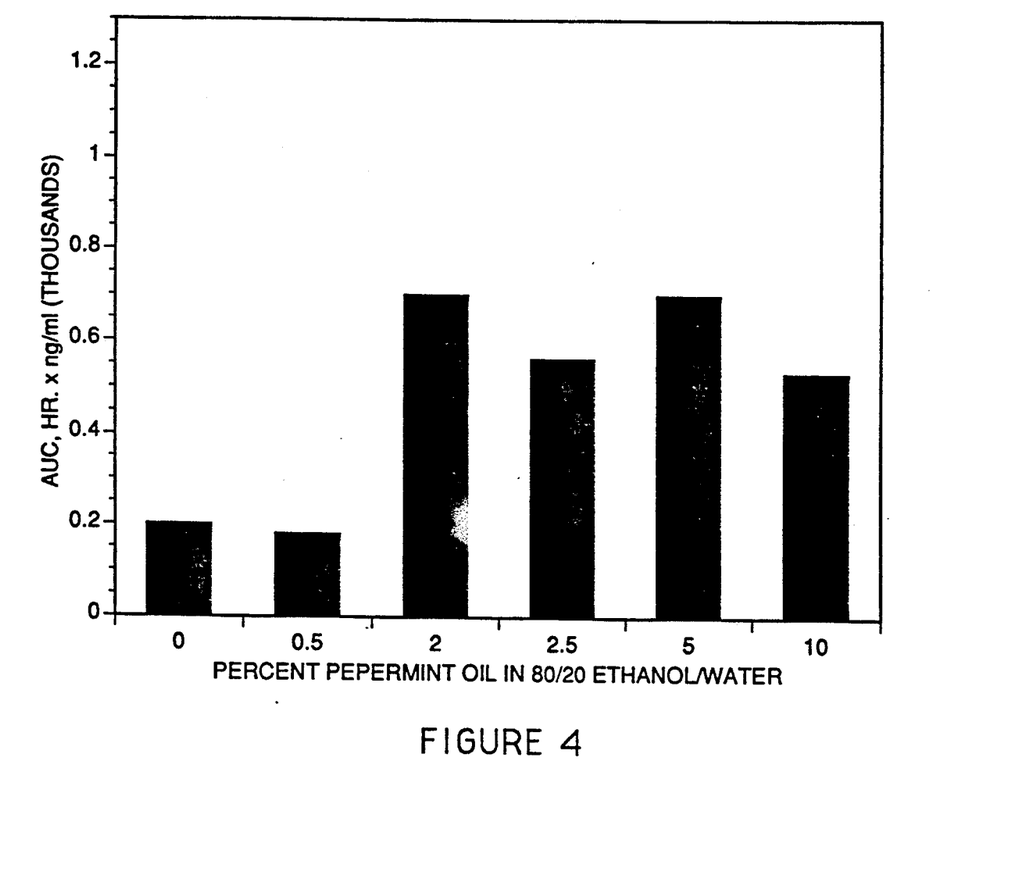
FIG. 4 is a bar graph of area under the curve (AUC 0–8 hours) vs. peppermint oil concentration (percent by volume). Dogs were sublingually administered 0.1 ml/10 kg body weight of a liquid composition comprising 50 mg/ml leuprolide acetate, an aqueous-alcohol solvent having 80 percent by volume ethanol and 0, 0.5, 2.0, 2.5, 5 or 10 percent by volume peppermint oil.

The data in FIG. 4 show that peppermint oil at a concentration of about 2 to 10 percent by volume increases the bioavailability of sublingually administered leuprolide acetate.

EXAMPLE 5

Bioavailability Of Sublinqually Administered Deslorelin

The synthetic polypeptide Deslorelin ™ (Sigma Chem Co., St. Louis, Mo.), pGlu-His-Trp-Ser-Tyr-D-TrpLeu-Arg-Pro-NHET (Sequence ID No. 4), was dissolved in either saline or a liquid composition comprising 2 percent by volume peppermint oil, 2.5 percent by weight Klucel LF™, 4 percent by weight benzoic acid and an aqueous-alcohol solvent having 65 percent by volume ethanol such that the concentration of Deslorelin ™ was about 68 mg/ml. About 0.1 ml of the Deslorelin ™ compositions were sublingually administered to anesthetized dogs and the plasma level of Deslorelin ™ measured by RIA immediately before and 0.33, 0.67, 1, 2, 3, 4, 6 and 8 hours after administration.

Where dogs received Deslorelin ™ in saline, the maximum plasma level observed was about 1.5 ng/ml and the AUC (0-8 hours) was about 2 hr-ng/ml. In marked contrast, dogs receiving Deslorelin ™ in a liquid composition of the present invention had a maximum plasma Deslorelin ™ level of about 290 ng/ml and an AUC (0-8 hours) of about 800 hr-ng/ml. These data show that a liquid composition of this invention markedly increases the bioavailability of sublingually administered Deslorelin ™.

We claim:

1. A pharmaceutical formulation for the sublingual or buccal administration of 5-oxoPro-His-Trp-Ser-Tyr-D-Leu-Arg-Pro-N-ethylamide Sequence ID No. 2) or pharmaceutically acceptable salt thereof comprising
   a) between 1 mg/ml and 100 mg/ml of said 5-oxoPro-His-Trp-Ser-Tyr-D-Leu-Arg-Pro-N-ethylamide or pharmaceutically acceptable salt thereof, and
   b) a pharmaceutically acceptable carrier comprising a cosolvent system comprising
      from about 50 percent w/v to about 95% w/v of an alcohol selected from the group consisting of ethanol, isopropanol, stearyl alcohol, propylene glycol and polyethylene glycol having a molecular weight of less than about 650 daltons, and
      from about 0.5 percent w/v to about 50 percent w/v of an oral mucosal membrane transport enhancing agent selected from the group consisting of peppermint oil, spearmint oil, menthol, pepper oil, eucalyptus oil, cinnamon oil, ginger oil, fennel oil, dill oil, hydrochloric acid, phosphoric acid, acetic acid, citric acid, lactic acid, oleic acid, linoleic acid, palmitic acid, benzoic acid, and salicylic acid; said percentages based upon the total volume of the carrier.

2. A pharmaceutical composition as defined by claim 1 wherein the carrier further comprises from about 5 percent w/v to about 50 percent w/v of a cosolvent selected from the group consisting of water or a pharmaceutically acceptable mineral or vegetable oil, based upon the volume of carrier.

3. A pharmaceutical composition as defined by claim 1 further comprising between about 0.1 and about 50 percent w/v of a hydrogel.

4. A pharmaceutical composition as defined by claim 1 wherein the alcohol is present in an amount ranging between about 55 percent w/v and about 80 percent w/v of the carrier.

5. A pharmaceutical composition as defined by claim 4 wherein the alcohol is selected from ethanol, propylene glycol, and poly(ethylene glycol) having a molecular weight of up to about 650 daltons.

6. A pharmaceutical composition as defined by claim 1 wherein said oral mucosal membrane transport enhancing agent comprises from about 2 percent w/v and about 20 percent w/v of said carrier.

7. A pharmaceutical composition as defined by claim 6 wherein said mucosal membrane transport enhancing agent is selected from the group consisting of peppermint oil, spearmint oil, menthol, pepper oil, eucalyptus oil, cinnamon oil, ginger oil, fennel oil, and dill oil.

8. The pharmaceutical composition as defined by claim 6 wherein said oral mucosal membrane transport enhancing agent is selected from the group consisting of hydrochloric acid, phosphoric acid, acetic acid, citric acid, lactic acid, oleic acid, linoleic acid, lauric acid, palmitic acid, benzoic acid, and salicylic acid.

9. A pharmaceutical composition as defined by claim 1 comprising
  a) between 1 mg/ml and 100 mg/ml of 5-oxoPro-His-Trp-Ser-Tyr-D-Leu-Arg-Pro-N-ethylamide or a pharmaceutically acceptable salt thereof;
  b) a carrier comprising
    1) between about 55 and about 80 percent w/v ethanol,
    2) about 2 to about 5 percent w/v of hydroxypropyl cellulose hydrogel; and
  c) between about 10 and about 25 percent w/v benzoic acid;
all percentages based upon the total volume of the carrier.

10. A pharmaceutical composition as defined by claim 9 comprising
  a) between 1 mg/ml and 100 mg/ml of 5-oxoPro-His-Trp-Ser-Tyr-D-Leu-Arg-Pro-N-ethylamide or a pharmaceutically acceptable salt thereof;
  b) a carrier comprising
    1) between about 55 and about 80 percent w/v ethanol,
    2) about 2 to about 5 percent w/v of hydroxypropyl cellulose hydrogel; and
  c) between about 5 and about 20 percent w/v benzoic acid and between about 1 to about 5 percent w/v peppermint oil;
all percentages based upon the total volume of the carrier.

11. A method of sublingually or bucally administering a therapeutic agent to a patient comprising the steps of:
  a) preparing a liquid pharmaceutical composition as defined by claim 1 and thereafter,
  b) administering the liquid composition of step 1 to the underside of the tongue of the patient.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Modified-site
        ( B ) LOCATION: 1
        ( D ) OTHER INFORMATION: /note="Xaa at position 1 is
            5-oxo- proline"

( i x ) FEATURE:
        ( A ) NAME/KEY: Modified-site
        ( B ) LOCATION: 10
        ( D ) OTHER INFORMATION: /note="Xaa at position 10 is
            glycinamide"

( x i ) SEQUENCE DESCRIPTION: SEQ ID NO:1:

```
Xaa His Trp Ser Tyr Gly Leu Arg Pro Xaa
1               5                   10
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Modified-site
        ( B ) LOCATION: 1
        ( D ) OTHER INFORMATION: /note="Xaa at position 1 is
            5-oxo- proline"

( i x ) FEATURE:
        ( A ) NAME/KEY: Modified-site
        ( B ) LOCATION: 6
        ( D ) OTHER INFORMATION: /note="Xaa at position 6 is
            D-leucine"

( i x ) FEATURE:
        ( A ) NAME/KEY: Modified-site
        ( B ) LOCATION: 9
        ( D ) OTHER INFORMATION: /note="Xaa at position 9 is
            proline-N- ethylamide"

( x i ) SEQUENCE DESCRIPTION: SEQ ID NO:2:

```
Xaa His Trp Ser Tyr Xaa Leu Arg Xaa
1               5
```

(2) INFORMATION FOR SEQ ID NO:3:

(i) SEQUENCE CHARACTERISTICS:
     (A) LENGTH: 32 amino acids
     (B) TYPE: amino acid
     (C) STRANDEDNESS: single
     (D) TOPOLOGY: linear (ii) MOLECULE TYPE: peptide (ix) FEATURE:
     (A) NAME/KEY: Modified-site
     (B) LOCATION: 26
     (D) OTHER INFORMATION: /note="xaa at position 26 is tyrosine-4- sulfonate"

(ix) FEATURE:
     (A) NAME/KEY: Modified-site
     (B) LOCATION: 32
     (D) OTHER INFORMATION: /note="Xaa at position 32 is phenylalaninamide"

(xi) SEQUENCE DESCRIPTION: SEQ ID NO:3:

```
Lys Ala Pro Ser Gly Arg Met Ser Ile Val Leu Asn Leu Gln Asn Leu
 1               5                  10                  15
Asp Pro Ser Arg Ile Ser Asp Arg Asp Xaa Met Gly Trp Met Asp Xaa
            20                  25                  30
```

(2) INFORMATION FOR SEQ ID NO:4:

(i) SEQUENCE CHARACTERISTICS:
     (A) LENGTH: 9 amino acids
     (B) TYPE: amino acid
     (C) STRANDEDNESS: single
     (D) TOPOLOGY: linear (ii) MOLECULE TYPE: peptide (ix) FEATURE:
     (A) NAME/KEY: Modified-site
     (B) LOCATION: 1
     (D) OTHER INFORMATION: /note="Xaa at position 1 is pyroglutamic acid"

(ix) FEATURE:
     (A) NAME/KEY: Modified-site
     (B) LOCATION: 6
     (D) OTHER INFORMATION: /note="Xaa at position 6 is D- tryptophan"

(ix) FEATURE:
     (A) NAME/KEY: Modified-site
     (B) LOCATION: 9
     (D) OTHER INFORMATION: /note="Xaa at position 9 is proline N- ethylamide"

(xi) SEQUENCE DESCRIPTION: SEQ ID NO:4:

```
Xaa His Trp Ser Tyr Xaa Leu Arg Xaa
 1               5
```